US012618784B2

(12) United States Patent
Meaney et al.

(10) Patent No.: US 12,618,784 B2
(45) Date of Patent: *May 5, 2026

(54) SYSTEMS AND METHODS FOR NON-INVASIVE MICROWAVE TESTING OF BOTTLES OF LIQUIDS, INCLUDING ALCOHOLIC BEVERAGES AND EDIBLE OILS LIKE OLIVE OIL

(71) Applicant: THE TRUSTEES OF DARTMOUTH COLLEGE, Hanover, NH (US)

(72) Inventors: Paul M. Meaney, Norwich, VT (US); Timothy Raynolds, Lebanon, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 148 days.

This patent is subject to a terminal disclaimer.

(21) Appl. No.: 18/627,833

(22) Filed: Apr. 5, 2024

(65) Prior Publication Data

US 2024/0345001 A1     Oct. 17, 2024

Related U.S. Application Data

(63) Continuation-in-part of application No. 17/264,961, filed as application No. PCT/US2019/044120 on Jul. 30, 2019, now Pat. No. 11,953,485.

(Continued)

(51) Int. Cl.
*G01N 22/00*        (2006.01)
*G01N 33/03*        (2006.01)
(Continued)

(52) U.S. Cl.
CPC ............. *G01N 22/00* (2013.01); *G01N 33/03* (2013.01); *G01N 33/146* (2013.01); *G01R 27/28* (2013.01)

(58) Field of Classification Search
CPC ...... G01N 22/00; G01N 33/03; G01N 33/146; G01N 21/3581; G01N 22/04; G01N 33/143; G01R 27/04; G01R 27/06; G01R 27/28

(Continued)

(56) References Cited

U.S. PATENT DOCUMENTS

| | | | |
|---|---|---|---|
| 7,319,212 B2 | 1/2008 | Godshalk et al. | |
| 2002/0014105 A1* | 2/2002 | Jakkula .................. | G01N 22/04 73/19.01 |

(Continued)

FOREIGN PATENT DOCUMENTS

| | | |
|---|---|---|
| WO | 9854586 A | 12/1998 |
| WO | 2012155057 A2 | 11/2012 |

OTHER PUBLICATIONS

International Patent Application No. PCT/US2019/044120, International Search Report and Written Opinion dated Oct. 25, 2019, 11 pgs.

*Primary Examiner* — Raul J Rios Russo
(74) *Attorney, Agent, or Firm* — Cozen O'Connor

(57) ABSTRACT

A system for non-invasive microwave testing a bottle of liquid may include an emission probe for emitting a microwave signal through a wall of the bottle into the liquid and a detection probe for receiving at least a portion of the microwave signal from the liquid via the wall. The system includes a classifier configured to distinguish olive oil from some other common vegetable oils, to distinguish real from some imitation maple syrups, and to distinguish between several alcoholic beverages.

14 Claims, 12 Drawing Sheets

Related U.S. Application Data

(60) Provisional application No. 62/711,689, filed on Jul. 30, 2018.

(51) Int. Cl.
  *G01N 33/14* (2006.01)
  *G01R 27/28* (2006.01)

(58) Field of Classification Search
  USPC ........................................................ 324/639
  See application file for complete search history.

(56) References Cited

U.S. PATENT DOCUMENTS

| | | | |
|---|---|---|---|
| 2004/0000653 A1 | 1/2004 | Nordlund | |
| 2007/0039950 A1* | 2/2007 | Godshalk | G01N 22/00 |
| | | | 219/679 |
| 2011/0184681 A1 | 7/2011 | Augustine et al. | |
| 2015/0097561 A1* | 4/2015 | Desmulliez | G01N 22/00 |
| | | | 324/300 |
| 2015/0247814 A1 | 9/2015 | Hofmann | |
| 2015/0293067 A1* | 10/2015 | Greene | G01N 33/0042 |
| | | | 356/72 |
| 2016/0018375 A1 | 1/2016 | Fahrni et al. | |
| 2016/0313260 A1 | 10/2016 | Meaney et al. | |
| 2019/0025228 A1 | 1/2019 | Muldoon | |
| 2020/0374679 A1 | 11/2020 | Agostinelli et al. | |
| 2021/0123786 A1* | 4/2021 | Pflüger | G01F 23/284 |
| 2022/0378338 A1* | 12/2022 | Castiñeira Moreira | ...................... |
| | | | A61B 5/6844 |
| 2023/0210414 A1* | 7/2023 | Connell | A61B 5/0507 |
| | | | 600/309 |

* cited by examiner

400

SYSTEMS AND METHODS FOR NON-INVASIVE MICROWAVE TESTING OF BOTTLES OF LIQUIDS, INCLUDING ALCOHOLIC BEVERAGES AND EDIBLE OILS LIKE OLIVE OIL

CROSS-REFERENCE TO RELATED APPLICATIONS

The present application is a Continuation-in-Part of U.S. application Ser. No. 17/264,961 filed Jul. 30, 2019 and expected to issue as U.S. Pat. No. 11,953,485 on Apr. 9, 2024, which is a 371 U.S. National Stage Entry of International Application No. PCT/US2019/044120 filed Jul. 30, 2019, which claims priority to U.S. Provisional Patent Application No. 62/711,689 filed Jul. 30, 2018. The entire contents of the aforesaid patent applications are incorporated herein by reference in their entirety.

BACKGROUND

Wine testing is used at wine production facilities, and also at higher-end restaurants and by individual wine enthusiasts. However, conventional wine testing methods generally require direct access to the wine and cannot be performed on wine inside closed bottles. Thus, for wine that has already been bottled, such conventional wine testing is necessarily invasive, and opening such bottled wine to detect counterfeit or defective wine drastically reduces its value.

In addition to wine, other liquids have significant value and are subject to counterfeiting or degradation. Among these are alcoholic beverages other than wine, such as but not limited to whiskeys, rums, vodkas, wine coolers, and others. Also frequently counterfeited or subject to degradation after bottling are high-end cooking oils such as but not limited to flaxseed oil and olive oil. Among adulterants used to extend or counterfeit olive oil are, but not limited to, sunflower oil, safflower oil, and soybean oil. Another sometimes-counterfeited liquid is pure maple syrup, for which many imitations are made with corn syrup.

One prior art method for non-invasive testing of wine in bottles utilizes nuclear magnetic resonance (NMR) spectroscopy to at least partly characterize the chemical composition of the wine. The NMR instrument is very expensive and large. Therefore, the NMR approach is not well-suited for small-scale wine testing at decentralized locations by restaurants, wine shops, or consumers.

Another prior art method uses a radio-frequency coil to measure dielectric properties of wine in bottles. The coil encircles the bottle and cooperates with electronics equipment to detect changes in the inherent resonance frequency of the wine at frequencies below 30 megahertz (MHz). This method requires significant electronics equipment. The interface with the bottle, e.g., the radio-frequency coil, must be large in order to encircle the bottle. In addition, wine bottle labels commonly have metallic print that interferes with the measurements and is likely to cause the measurement to fail.

SUMMARY

In an embodiment, a system for non-invasive microwave testing a bottle of liquid may include an emission probe for emitting a microwave signal through a wall of the bottle into the liquid and a detection probe for receiving at least a portion of the microwave signal from the liquid via the wall. The system includes a classifier configured to distinguish olive oil from some other common vegetable oils, to distinguish real from some imitation maple syrups, and to distinguish between several alcoholic beverages.

In an embodiment, a system for non-invasive microwave testing a bottle of wine includes (a) an emission probe for emitting a microwave signal through a wall of the bottle into the wine and (b) a detection probe for receiving at least a portion of the microwave signal from the wine via the wall.

In an embodiment, a method for non-invasive microwave testing a bottle of wine may include (a) emitting, from an emission probe coupled to a wall of the bottle, a microwave signal through the wall and into the wine and (b) receiving, from the wine via the wall, at least a portion of the microwave signal into a detection probe coupled to the wall.

DETAILED DESCRIPTION OF EXAMPLE EMBODIMENTS

Figure 1:
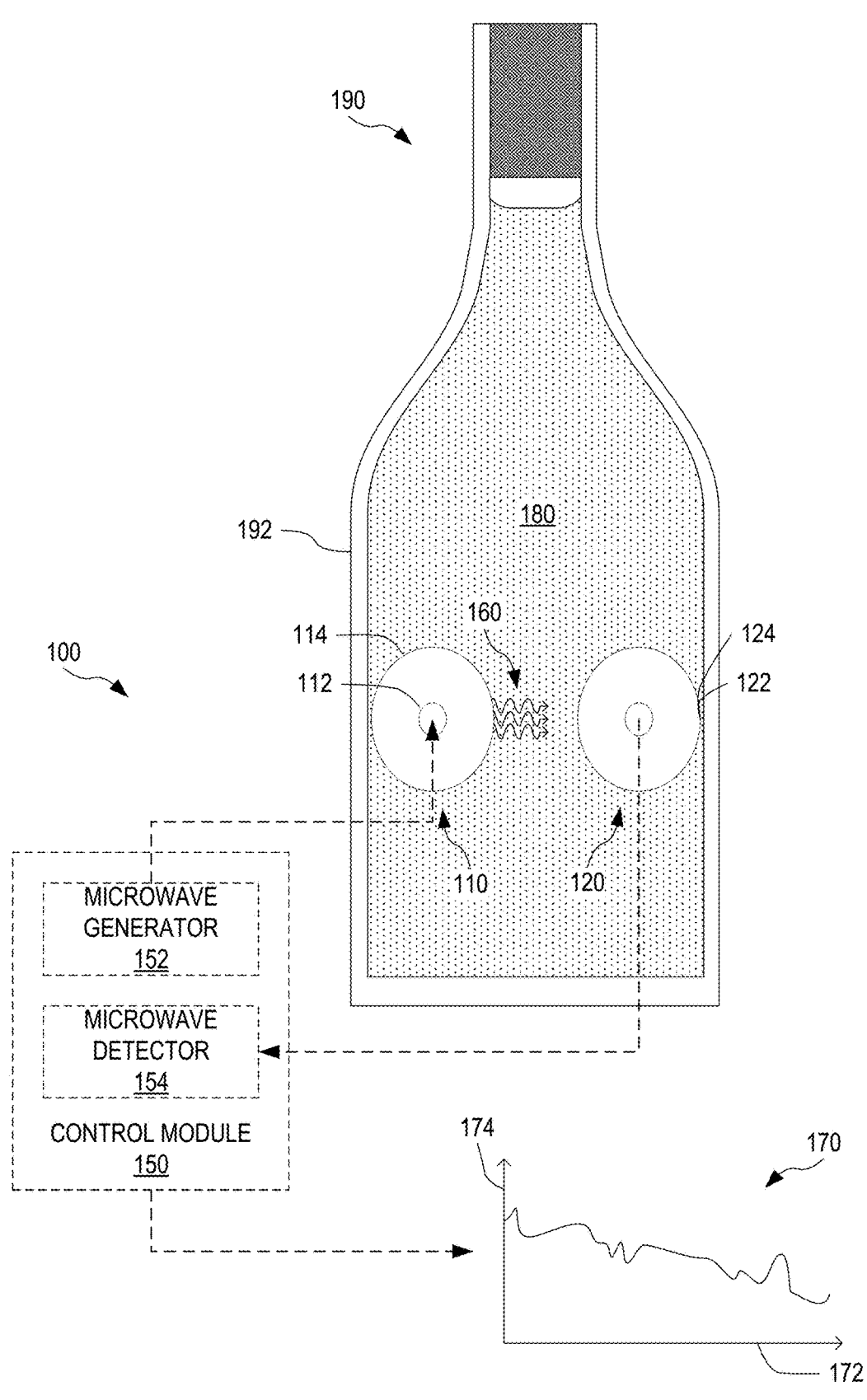
FIG. 1 illustrates a system a for non-invasive microwave testing of bottles of wine, according to an embodiment.

FIG. 1 illustrates one system 100 for non-invasive microwave testing of bottles 190 of wine 180. System 100 interrogates wine 180 through a wall 192 of bottle 190 and does not require opening of bottle 190 or physically penetrating a seal (e.g., cork or cap) of bottle 190. System 100 includes an emission probe 110 and a detection probe 120.

In operation, emission probe 110 and detection probe 120 are coupled to an outside surface of wall 192, emission probe 110 emits a microwave signal 160 through wall 192 and into wine 180, and detection probe 120 receives at least a portion of microwave signal 160 after propagation in wine 180. Microwave signal 160 is, for example, in the range between 0.3 Gigahertz and 300 Gigahertz or in the range between 1 Gigahertz and 30 Gigahertz. Neither emission probe 110 nor detection probe 120 spans around the entire circumference of bottle 190. Thus, emission probe 110 and detection probe 120 may be made smaller than a probe that fully surrounds bottle 190. Furthermore, for bottles 190 having labels with metallic print, emission probe 110 and detection probe 120 may be coupled to wall 192 in places without metallic print.

Each of emission probe 110 and detection probe 120 is a coaxial probe. Emission probe 110 includes a center conductor 112 and an outer conductor 114. Detection probe 120 includes a center conductor 122 and an outer conductor 124. Emission probe 110 and detection probe 120 may be identical and interchangeable.

System 100 may include a control module 150 having a microwave generator 152 and a microwave detector 154. Microwave generator 152 sends a microwave signal 160 to emission probe 110, causing emission probe to emit microwave signal 160 into wine 180. Microwave signals received by detection probe 120 are relayed to microwave detector 154. It is understood that microwave signal 160 may be subject to attenuation and/or reflection losses between microwave generator 152 and wine 180, and that the portion of microwave signal 160 received by detection probe 120 may be subject to attenuation and/or reflection losses between detection probe 120 and microwave generator 152.

In one scenario, control module 150 (a) scans the frequency of microwave signal 160 outputted by microwave generator 152 and (b) uses microwave detector 154 to record a spectrum 170 of the corresponding microwave signal received by detection probe 120. Spectrum 170 may be a magnitude spectrum that indicates the magnitude of the received microwave signal (on axis 174) as a function of microwave frequency (on axis 172). The magnitude spectrum may be normalized to the magnitude of microwave signal 160 outputted by microwave generator 152. Alternatively, spectrum 170 may be a phase spectrum that indicates the phase of the received microwave signal relative to the phase of microwave signal 160 as a function of the microwave frequency. In certain scenarios, control module 150 generates both a magnitude spectrum and a phase spectrum. Spectral features of the magnitude spectrum and/or the phase spectrum may be used to determine a property of wine 180. For example, a recorded spectrum for a given type of wine 180 may be compared to a reference spectrum for that wine. Differences between the recorded spectrum and the reference spectrum may indicate aging of wine 180, undesirable decay of wine 180, contamination of wine 180, or that the wine 180 is counterfeit.

To effectively couple microwave signal 160 from emission probe 110 to wine 180 and effectively couple at least a portion of microwave signal 160 from wine 180 to detection probe 120, each of emission probe 110 and detection probe 120 is made to substantially match the curvature of wall 192. In one implementation, the end face of each of emission probe 110 and detection probe 120 has a curvature that substantially matches the curvature of wall 192. For example, the end face may be cylindrical with a radius of curvature in the range between 1.5 and 2.5 inches. A coupling medium, such as a gel (e.g., a water-based gel), may be used to compensate for deviations between the curvature of wall 192 and the end face of either one of emission probe 110 and detection probe 120, at least when such deviations are minor. In another implementation, each of emission probe 110 and detection probe 120 is flexible and capable of conforming to the curvature of wall 192, at least one a cylindrical portion of wall 192. In certain embodiments, compatible with typical bottles 190, the end face of each of emission probe 110 and detection probe 120 is cylindrical.

Figure 2:
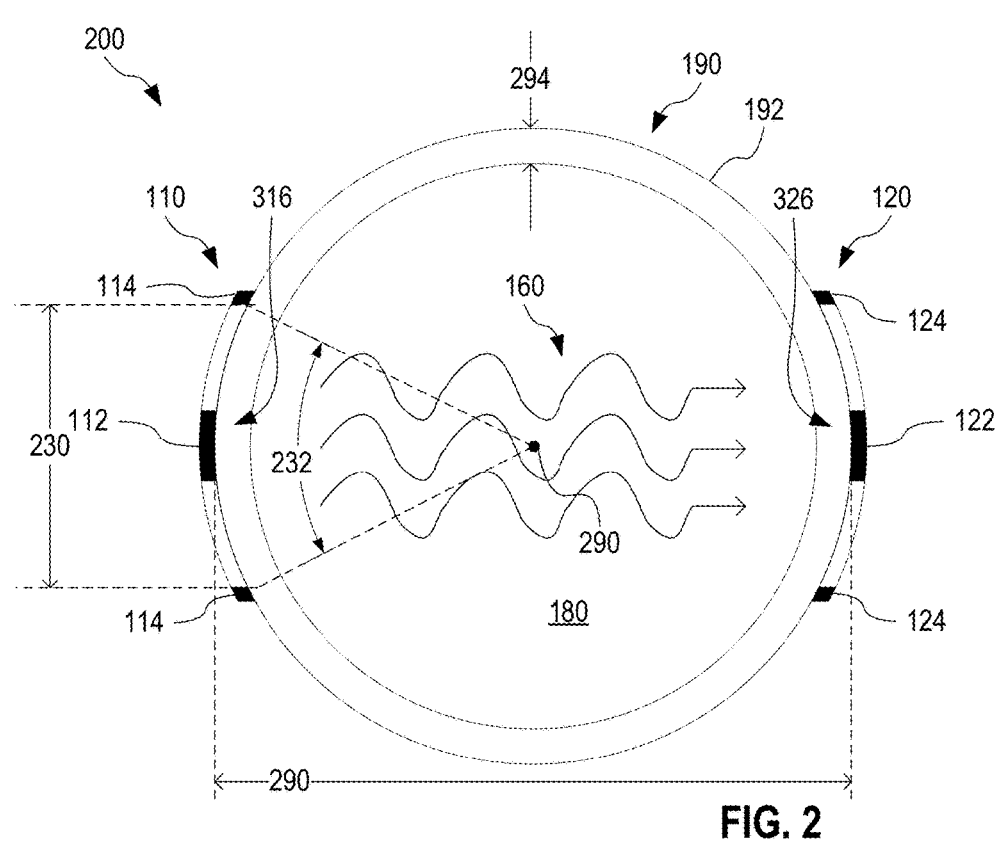
FIG. 2 illustrates a transmission-based configuration of the system of FIG. 1, according to an embodiment.

FIG. 2 illustrates one transmission-based configuration 200 of system 100. FIG. 2 shows a cross sectional view of bottle 190 with emission probe 110 and detection probe 120 coupled thereto, wherein the cross section is orthogonal to a height axis 290 of bottle 190. In configuration 200, emission probe 110 and detection probe 120 are coupled to opposite sides of wall 192, such that an end face 326 of detection probe 120 faces an end face 316 of emission probe 110. Microwave signal 160 may be transmitted through wine 180 from emission probe 110 to detection probe 120 (via two passes through wall 192). Wall 192 has a thickness 294. It is understood that one or both of emission probe 110 and detection probe 120 may extend further away from wall 192 than depicted in FIG. 2.

Each of emission probe 110 and detection probe 120 may include a transmission line to the respective one of end faces 316 and 326. For example, in one class of embodiments, the center conductor and outer conductor extends away from the end face to form a coaxial transmission line (see, e.g., FIGS. 5A-C, 6A-C, 7A and 7B). In another class of embodiments, probe 110/120 is planar and includes a planar transmission line (see, e.g., FIGS. 10-14).

We have found that, the strength of microwave signal 160 received by detection probe 120 increases with the value of diameter 230. Diameter 230 corresponds to an angle 232 with respect to height axis 290 and along the circumference of wall 192. In one embodiment, angle 232 is at least 40 degrees. In another embodiment, suitable for instances of wall 192 having a diameter approximately in the range between 3.5 and 4.5 inches, diameter 230 is at least 1.0 inches, for example between 1.0 and 1.5 inches.

As an alternative configuration, consider a reflection-based measurement, wherein a single probe (e.g., emission probe 110) is used for both emission and detection of microwave signal 160. However, reflection-based measurements are challenged by a shallow 1/e penetration depth of microwave signal 160 into bottle 190. Even for probes characterized by angle 232 being at least 40 degrees or diameter 230 being at least 1.0 inches, the 1/e penetration depth into bottle 190 may be as shallow as 4-5 millimeters. Therefore, in such a reflection-based measurement, a relatively large fraction of the reflected microwave signal may be reflected already in wall 192 immediately adjacent to the probe or after propagating only a relatively short distance in wine 180. As a result, the reflected microwave signal may be dominated by a contribution that has had no or only very little interaction with the wine 180. Thus, it may be difficult to derive information about wine 180 from such reflection measurements. In contrast, in configuration 200, the portion of microwave signal 160 received by detection probe 120 has propagated across essentially the full width of bottle 190. Although microwave signal 160 may be greatly attenuated before reaching detection probe 120, the portion of microwave signal 160 that actually does reach detection probe 120 is strongly affected by the properties of wine 180. The measurements of the detected microwave signal 160 may therefore serve as a relatively reliable indicator of properties of wine 180. For example, spectral features of spectra 170 may be attributed to actual properties of wine 180 with significantly greater confidence than in a reflection-based measurement.

One potential drawback to configuration 200 is susceptibility to signal corruption caused by multipath interference from propagation paths that entirely or mostly circumvent wine 180. For example, a portion of microwave signal 160 may propagate from emission probe 110 to detection probe 120 along the interface between wall 192 and wine 180 rather than through wine 180. Since the signal loss for propagation paths through wine 180 may be similar to the signal loss for propagation paths along the interface between wall 192 and wine 180, the portion of microwave signal 160 received by detection probe 120 may be affected by multipath interference.

Figure 3:
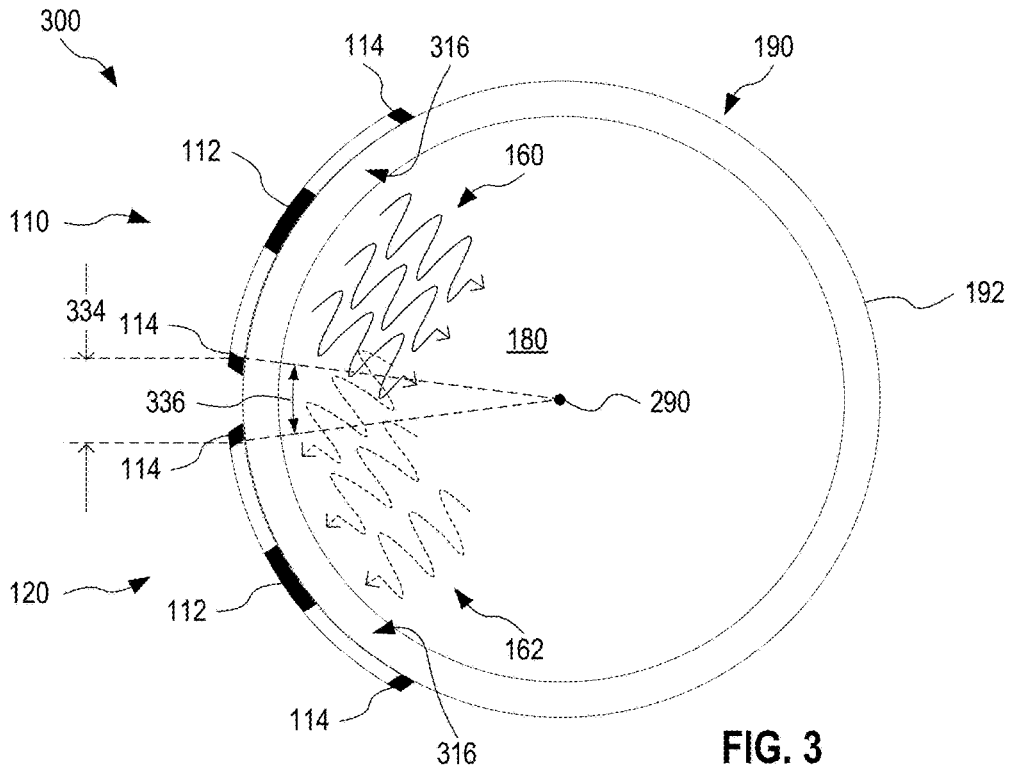
FIG. 3 illustrates a side-by-side configuration of the system of FIG. 1, according to an embodiment.

FIG. 3 illustrates a side-by-side configuration 300 of system 100, wherein emission probe 110 and detection probe 120 are positioned side by side. FIG. 2 shows a cross sectional view of bottle 190 with emission probe 110 and detection probe 120 coupled thereto, wherein the cross section is orthogonal to a height axis 290 of bottle 190. In configuration 300, end face 316 of emission probe 110 and end face 326 of detection probe 120 are positioned on a same half of the circumference of wall 192. As a result, detection probe 120 receives a portion 162 of microwave signal 160 that is at least predominantly reflected/scattered by wine 180, as opposed to directly transmitted through wine 180.

The shortest distance 334 between the inside diameter of outer conductor 114 of emission probe 110 and the inside diameter of outer conductor 114 of detection probe 120 may be less than 0.5 inches, for example in the range between 5 and 12 millimeters. Distance 334 corresponds to an angle 336 between emission probe 110 and detection probe 120. Angle 336 may be less than 15 degrees.

The propagation path of portion 162 from emission probe 110 to detection probe 120 in configuration 300 may be somewhat shorter than the possible propagation paths of microwave signal 160 between emission probe 110 and detection probe 120 in configuration 200, such that portion 162 is less affected by wine 180 than the portion of microwave signal 160 reaching detection probe 120 in configuration 200. On the other hand, the side-by-side configuration of emission probe 110 and detection probe 120 in configuration 300 ensures that the propagation paths of portion 162 from emission probe 110 to detection probe 120 in configuration 300 are longer than the propagation paths that dominate the signal in a single-probe reflection-based configuration. In addition, by virtue of emission probe 110 and detection probe 120 being close to each other, configuration 300 is expected to be far less susceptible to signal corruption from multipath interference. For example, the propagation paths from emission probe 110 through wine 180 to detection probe 120 are generally much longer than the most immediate propagation path, along the interface between wall 192 and wine 180, across the shortest gap between emission probe 110 and detection probe 120.

While FIG. 3 shows emission probe 110 and detection probe 120 as being offset from each other in the azimuthal direction relative to height axis 290 of bottle 190, emission probe 110 and detection probe 120 may instead, in an alternative configuration, be offset from each other in a direction that is parallel to height axis 290 of bottle 190.

Figure 4:
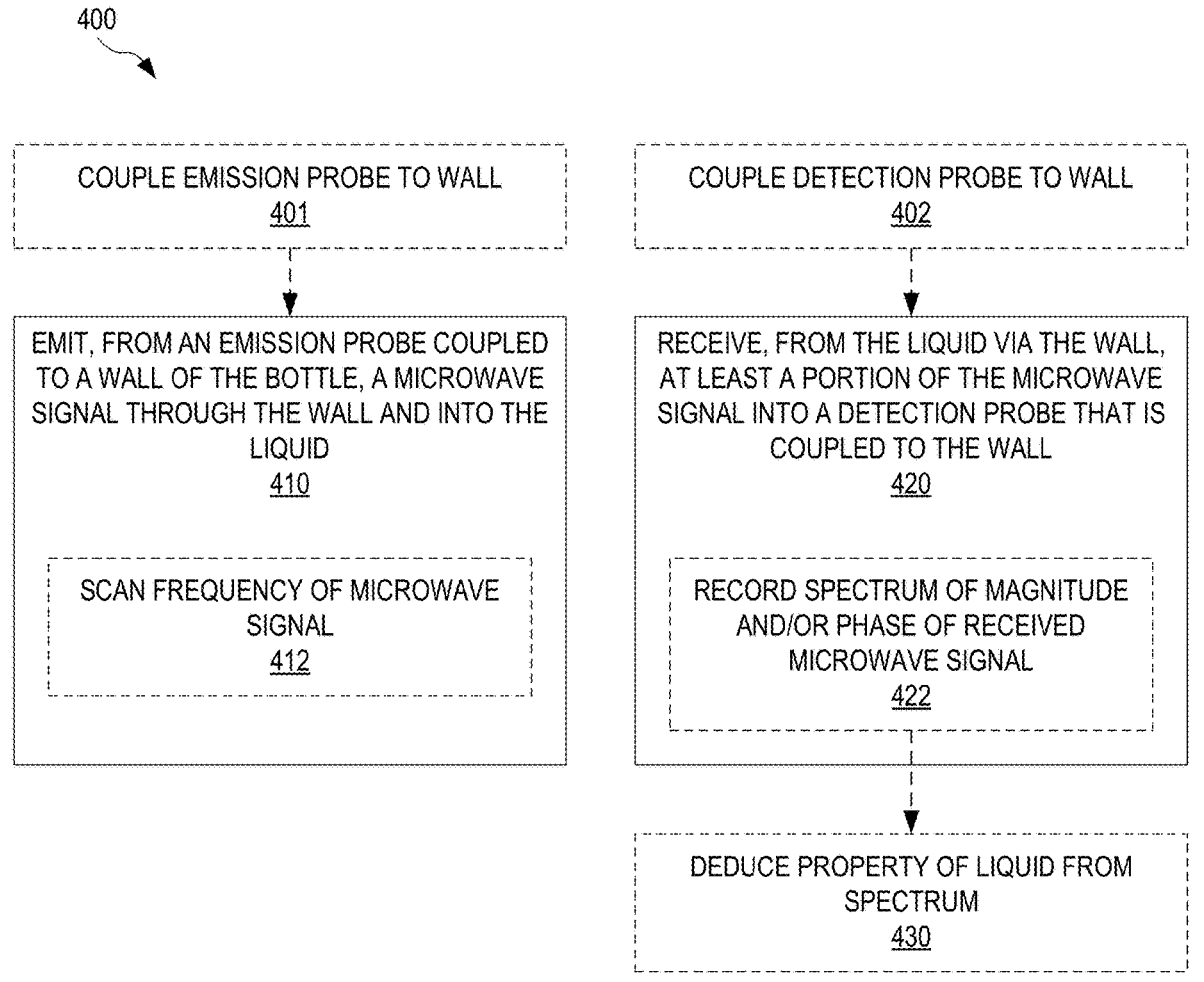
FIG. 4 illustrates a method for non-invasive microwave testing of a bottle of liquid, according to an embodiment.

FIG. 4 illustrates one method 400 for non-invasive microwave testing of a bottle of liquid, which in a particular embodiment is wine. Method 400 may be performed by system 100 using any one of the emission/detection probe pairs and associated configurations disclosed herein. Method 400 includes steps 410 and 420 that are performed concurrently. In step 410, an emission probe coupled to a wall of the bottle emits a microwave signal through the wall and into the liquid. In one example of step 410, emission probe 110 emits microwave signal 160 through wall 192 into liquid 180, as discussed above in reference to FIGS. 1-3. In step 420, a detection probe coupled to the wall of the bottle receives, from the liquid and through the wall, at least a portion of the microwave signal emitted in step 410. The emission and detection probes may be identical. However, method 400 uses separate probes for emission and detection. In one example of step 420, detection probe 120 receives at least a portion of microwave signal 160 from liquid 180 through wall 192.

In one embodiment, step 410 includes a step 412 of scanning the frequency of the microwave signal, and step 420 includes a step 422 of recording a spectrum of the magnitude and/or phase of the received microwave signal. In one example of this embodiment, control module 150 (a) scans the frequency of microwave signal 160 outputted by microwave generator 152 and (b) records one or more spectra 170 of a portion of microwave signal 160 detected by microwave detector 154, as discussed above in reference to FIG. 1. In one implementation, control module 150 records both a magnitude spectrum and a phase spectrum. The embodiment of method 400 that includes steps 412 and 422 may further include a step 430 of deducing a property of the wine, as discussed above in reference to FIG. 1.

Steps 410 and 420 may be preceded by steps 401 and 402, respectively. Step 401 couples the emission probe to the wall, and step 402 couples the detection probe to the wall. In one example of step 401, a user or a robot couples emission probe 110 to wall 192. In one example of step 402, a user or a robot couples detection probe 120 to wall 192. Each of steps 401 and 402 may include placing a coupling medium between the wall and the end face of the respective probe, for example when the curvature of the end face deviates somewhat from the curvature of the wall, or when the surface of either one of the end face and the wall has irregularities. The coupling medium may include a water-based gel. The water-based gel may be provided in a fabric that is placed between the end face and the wall. For flexible probes, each of steps 401 and 402 may include bending the probe until the end face of the probe conforms to the wall.

Figure 5A:
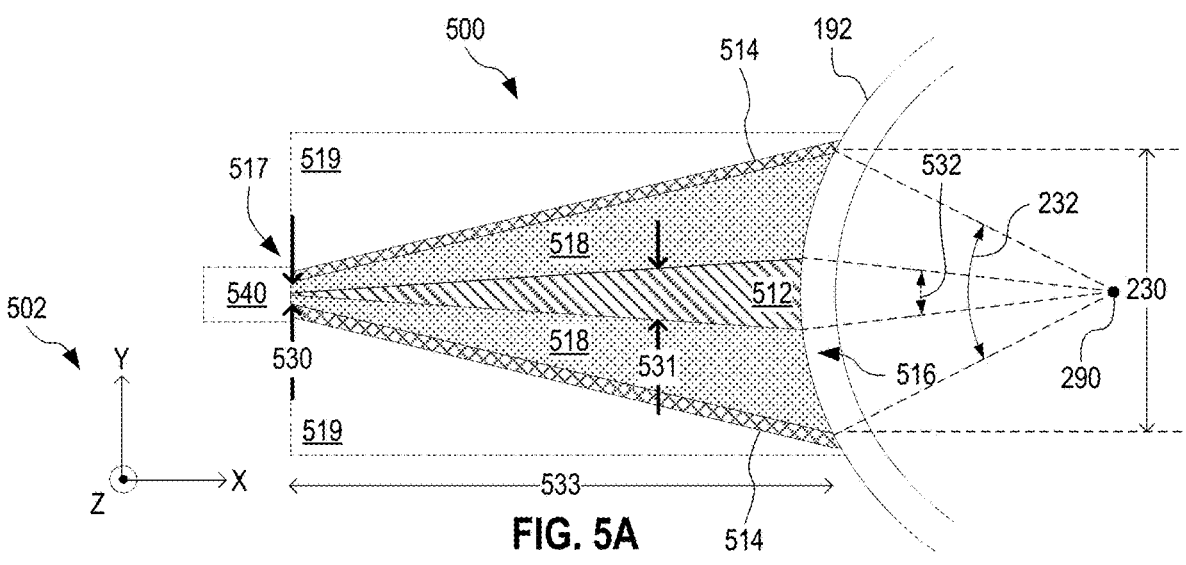
FIGS. 5A-C illustrate a tapered coaxial probe, according to an embodiment.
Figure 5B:
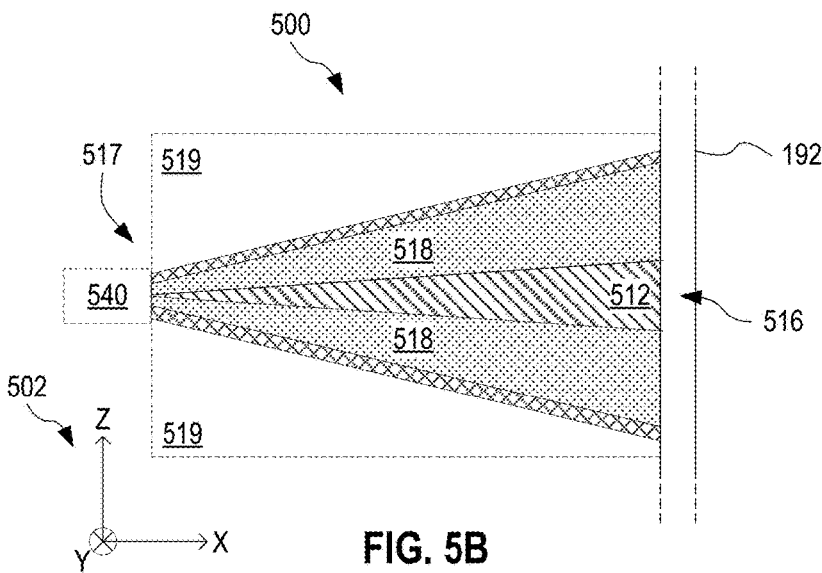
Figure 5C:
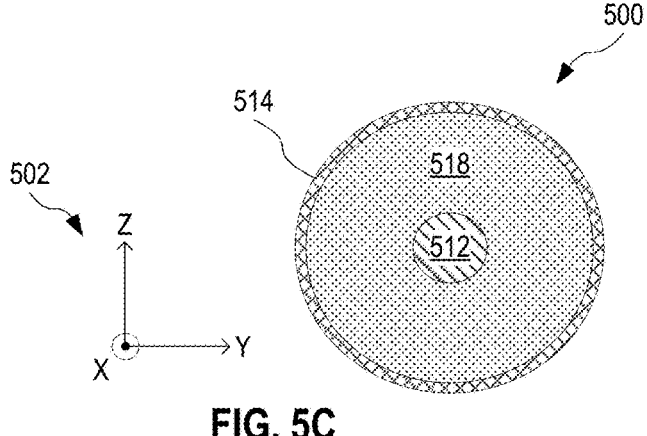

FIGS. 5A-C illustrate one tapered coaxial probe 500. Probe 500 is an embodiment of either one of emission probe 110 and detection probe 120. For example, one embodiment of system 100 implements each of emission probe 110 and detection probe 120 as probe 500. FIG. 5A is a cross-sectional view of probe 500 when an end face 516 thereof is coupled to wall 192 of bottle 190, wherein the cross section is orthogonal to height axis 290 of bottle 190. FIG. 5B is a cross-sectional view of probe 500 coupled to wall 192 of bottle 190 when end face 516 is coupled to wall 192, wherein the cross section is parallel to height axis 290 of bottle 190. FIG. 5C is a view of an end face 516 of probe 500. FIGS. 5A-C are best viewed together in the following description. For reference, each of FIGS. 5A-C shows a cartesian coordinate system 502 having its z-axis parallel to height axis 290 of bottle 190.

Probe 500 includes a center conductor 512, an outer conductor 514, and an insulator 518 therebetween. Center conductor 512 and outer conductor 514 may be made of metal. Insulator 518 may be a polymer, such as a polymer composed of or including polytetrafluoroethene. Probe 500 may be rigid. End face 516 is cylindrical, so as to match the shape of wall 192 at a typical cylindrical portion of bottle 190. At end face 516, insulator 518 spans angle 232, and center conductor 512 spans a corresponding angle 532. Angle 532 is between 5 and 20 degrees, for example.

At end face 516, the inside diameter of outer conductor 514 (corresponding to the outside diameter of insulator 518) equals diameter 230. However, in the direction from end face 516 to a back end 517 of probe 500, the inside diameter of outer conductor 514 tapers from diameter 230 to a smaller diameter 530. In other words, probe 500 forms a tapered coaxial transmission line with a diameter that increases from back end 517 to end face 516. The diameter 531 of center conductor 512 may taper at a rate proportional to the taper of outer conductor 514 from diameter 230 to diameter 530. The distance between center conductor 512 and outer conductor 514 may increase from back end 517 to end face 516. Diameter 530 may be compatible with a standard coaxial cable connector, such as a Type-N connector, a Bayonet Neill-Concelman (BNC) connector, or a Threaded Neill-Concelman (TNC) connector. In one embodiment, diameter 530 is in the range between 5 and 15 millimeters. Probe 500 may include a connector 540 at back end 517. Connector 540 may be a Type-N connector, a BNC connector, or a TNC connector. The axial distance 533 from end face 516 (where the inside diameter of outer conductor 514 equals diameter 230) to back end 517 is, for example, in the range between 2 and 6 inches.

Although FIGS. 5A and 5B depict outer conductor 514 as having constant thickness, outer conductor 514 may have varying thickness and, for example, extend farther from insulator 518 than depicted in FIGS. 5A-C. For example, outer conductor 514 may be a solid block that occupies area 519 indicated in FIGS. 5A and 5B.

In embodiments of method 400 that utilize probe 500, steps 401 and 402 may include placing a coupling medium between end face 516 and wall 192, as discussed above in reference to FIG. 4.

Figures 6A, 6B, 6C:
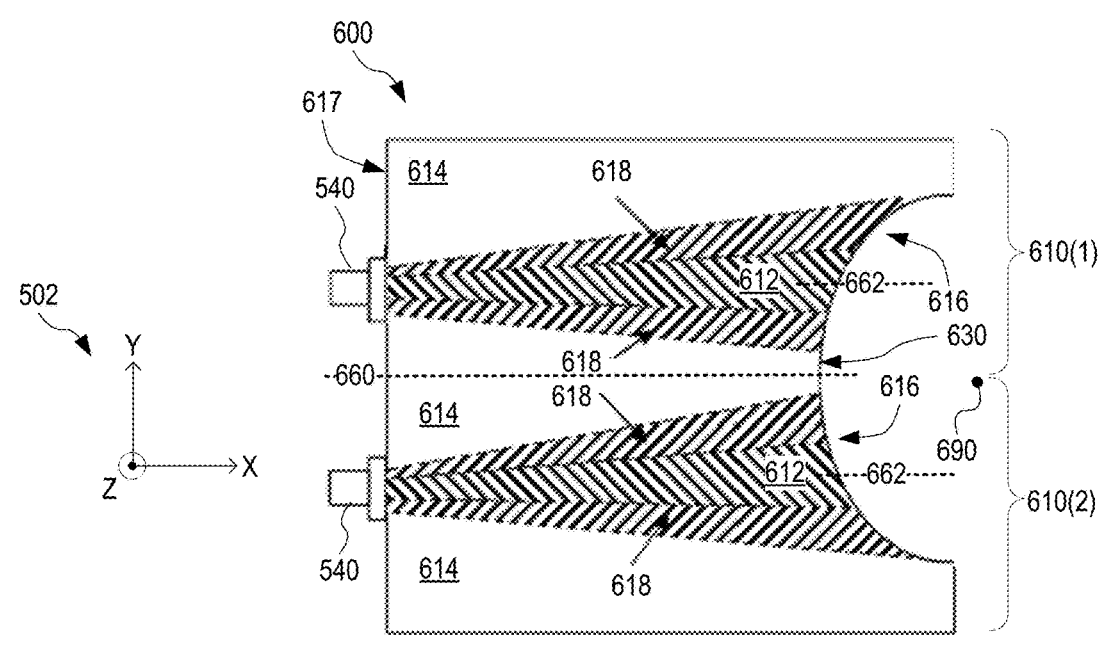
FIGS. 6A-C illustrate a dual-coaxial probe assembly having two side-by-side tapered coaxial probes, according to an embodiment.

FIGS. 6A-C illustrate one dual-coaxial probe assembly 600 having two side-by-side tapered coaxial probes 610. Probe assembly 600 is an embodiment of emission probe 110 and detection probe 120 of system 100 implemented according to configuration 300. FIGS. 6A and 6B are orthogonal cross-sections of probe assembly 600. FIG. 6C is a view of an end of probe assembly 600 forming a cylindrical surface 630 configured to couple with a cylindrical portion of wall 192 of bottle 190. FIGS. 6A-C are best viewed together in the following description. For reference, each of FIGS. 6A-C indicates the orientation of probe assembly 600, when coupled to wall 192, relative to coordinate system 502 having its z-axis parallel to height axis 290 of bottle 190.

Probe assembly 600 includes two center conductors 612. Each center conductor 612 is surrounded by an insulator 618. Probe assembly 600 further includes a conductive block 614. Conductive block 614 forms cylindrical surface 630 and a back surface 617, facing away from cylindrical surface 630. Conductive block 614 further forms two conical channels. Each conical channel is occupied by one center conductor 612 and its surrounding insulator 618, such that insulator 618 separates center conductor 612 from conductive block 614. Each center conductor 612 and its surrounding insulator 618 cooperates with conductive block 614 to form a respective probe 610. For each probe 610, conductive block 614 functions as its outer conductor.

Center conductors 612 and conductive block 614 may be made of metal. Insulators 618 may be made of a polymer, such as a polymer composed of or including polytetrafluoroethene. Probe assembly 600 may be rigid.

Probes 610(1) and 610(2) form mirror images of each other when reflected in a plane 660 (see FIG. 6A) that contains a cylinder axis 690 corresponding to cylindrical surface 630. An axis 662 of each probe 610 is parallel to plane 660 and extends generally along the x-axis of coordinate system 502 (see FIG. 6B). Without departing from the scope hereof, axes 662 of probe 610(1) and 610(2) may deviate from being parallel to plane 660 and/or each other. In certain embodiments, axes 662 of probe 610(1) and 610(2) are within ten degrees of being parallel to each other. In one such embodiment, axis 662 of probe 610(1) is at an angle of up to five degrees relative to plane 660 so as to be slightly more aimed at cylinder axis 690, while axis 662 of probe 610(2) is similarly at an angle of up to five degrees relative to plane 660 so as to be slightly more aimed at cylinder axis 690. In another such embodiment, axis 662 of each probe 610 is aimed directly toward cylinder axis 690.

Also without departing from the scope hereof, probes 610(1) and 610(2) may be on opposite sides of plane 660 without forming mirror images of each other. For example, axes 662 of probes 610(1) and 610(2) may be at two opposite oblique angles to the x-y plane of coordinate system 502, such that one probe 610 would point in a downwards direction from left to right in the FIG. 6B view while another probe 610 would point in an upwards direction from left to right in the FIG. 6B view.

Each probe 610 has an end face 616 that follows the contour of cylindrical surface 630. At end face 616, center conductor 612 and insulator 618 may have dimensions similar to those of center conductor 512 and insulator 518 of probe 500 at end face 516. At back surface 617, each probe 610 may have dimensions similar to the corresponding dimensions of probe 500 at back end 517. Each probe 610 forms a tapered coaxial transmission line from its end face 616 to back surface 617. In an embodiment, each center conductor 612 is tapered from end face 616 to back surface 617, in a manner similar to the tapering of center conductor 512 of probe 500. The axial distance of each probe 610 from cylindrical surface 630 to back surface 617 may be similar to axial distance 533. The extent of conductive block 614 may differ from that depicted in FIGS. 6A-C. For example, conductive block 614 may be truncated in regions away from insulators 618.

For ease of placing probe assembly 600 on bottle 190, cylindrical surface 630 may be configured to extend no more than 180 degrees about cylinder axis 690. In such embodiments, probe assembly 600 may be brought into contact with bottle 190 by approaching bottle 190 from the side. In the example depicted in FIG. 6A, cylindrical surface 630 extends approximately 180 degrees about cylinder axis 690. In an alternative embodiment, cylindrical surface 630 extends more than 180 degrees about cylinder axis 690. In this alternative embodiment, probe assembly 600 must be coupled onto bottle 190 by sliding probe assembly 600 onto bottle 190 along its height axis 290.

Each probe 610 may include a corresponding instance of connector 540 at back surface 617.

In embodiments of method 400 that utilize probe assembly 600, steps 401 and 402 are performed simultaneously and may include placing a coupling medium between cylindrical surface 630 and wall 192, as discussed above in reference to FIG. 4.

Figure 7A:
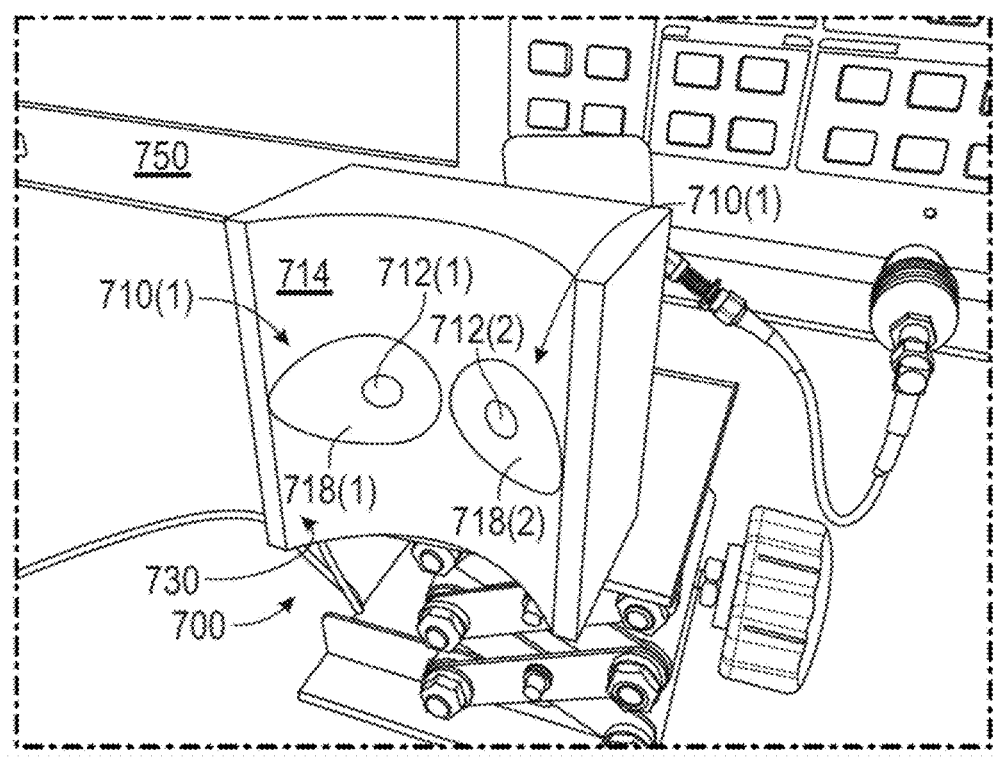
FIGS. 7A and 7B show a dual-coaxial probe assembly having two side-by-side tapered coaxial probes, according to an embodiment.
Figure 7B:
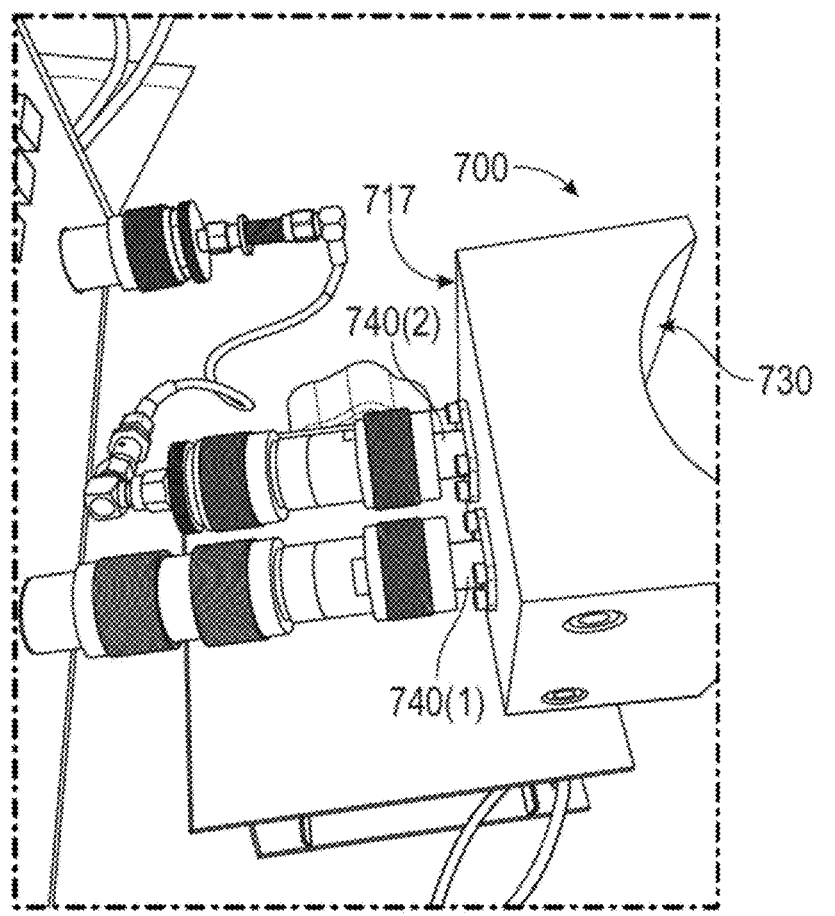

FIGS. 7A and 7B show two perspective views of one dual-coaxial probe assembly 700 having two side-by-side tapered coaxial probes 710. FIGS. 7A and 7B are best viewed together in the following description. Probe assembly 700 is an embodiment of probe assembly 600 and is depicted in FIGS. 7A and 7B as being connected to a spectrum analyzer 750. Spectrum analyzer 750 is an embodiment of microwave generator 152 and microwave detector 154. Spectrum analyzer 750 may form an embodiment of control module 150. Alternatively, spectrum analyzer 750 may be at least partly controlled by an external computer and cooperate with this external computer to form an embodiment of control module 150.

Probe assembly 700 includes two metal center conductors 712 surrounded by polytetrafluoroethene insulators 718. Probe assembly 700 further includes a metal block 714 forming (a) a cylindrical surface 730 (b) a planar back surface 717 facing away from cylindrical surface 730, and (c) two conical channels, each of which spans from cylindrical surface 730 to planar back surface 717 and is occupied by a respective center conductor 712 and its surrounding insulator 718.

Probe assembly 700 also includes two Type-N connectors 740, each connected to a respective center conductor 712 and metal block 714. Connector 740(1) is connected, via a standard coaxial cable, to an output of spectrum analyzer 750 and connector 740(2) is connected, via a standard coaxial cable, to an input of spectrum analyzer 750. Thus, in the setup depicted in FIGS. 7A and 7B, the probe associated with center conductor 712(1) functions as an emission probe, and the probe associated with center conductor 712 (2) functions as a detection probe.

Figure 8:
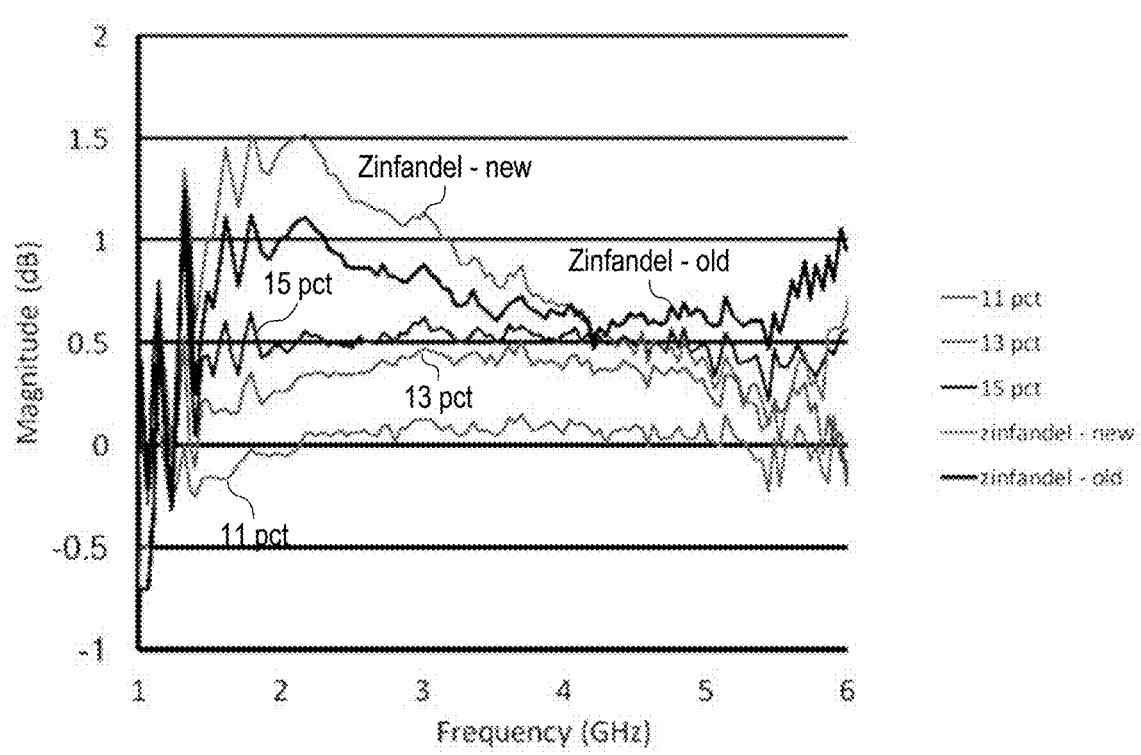
FIG. 8 is a plot of magnitude spectra obtained using the probe assembly of FIGS. 7A and 7B.

FIG. 8 is a plot of magnitude spectra obtained using probe assembly 700 and spectrum analyzer 750. The spectra plotted in FIG. 8 are examples of spectrum 170. FIG. 8 plots, for different types of liquids in a bottle, the microwave magnitude detected by spectrum analyzer 750, via the probe associated with center conductor 712(2), as a function of the frequency of the microwave signal outputted by spectrum analyzer 750 via the probe associated with center conductor 712(1). The different liquids tested are new Zinfandel wine, old Zinfandel wine, water with 11 percent ethanol, water with 13 percent ethanol, and water with 15 percent ethanol. Although some features are shared between the different types of liquids, it is clear that different liquids have different magnitude spectra. For example, the behavior of old Zinfandel wine is easily distinguished from that of new Zinfandel wine, and both Zinfandel wines are markedly different from all water/ethanol solutions.

Figure 9:
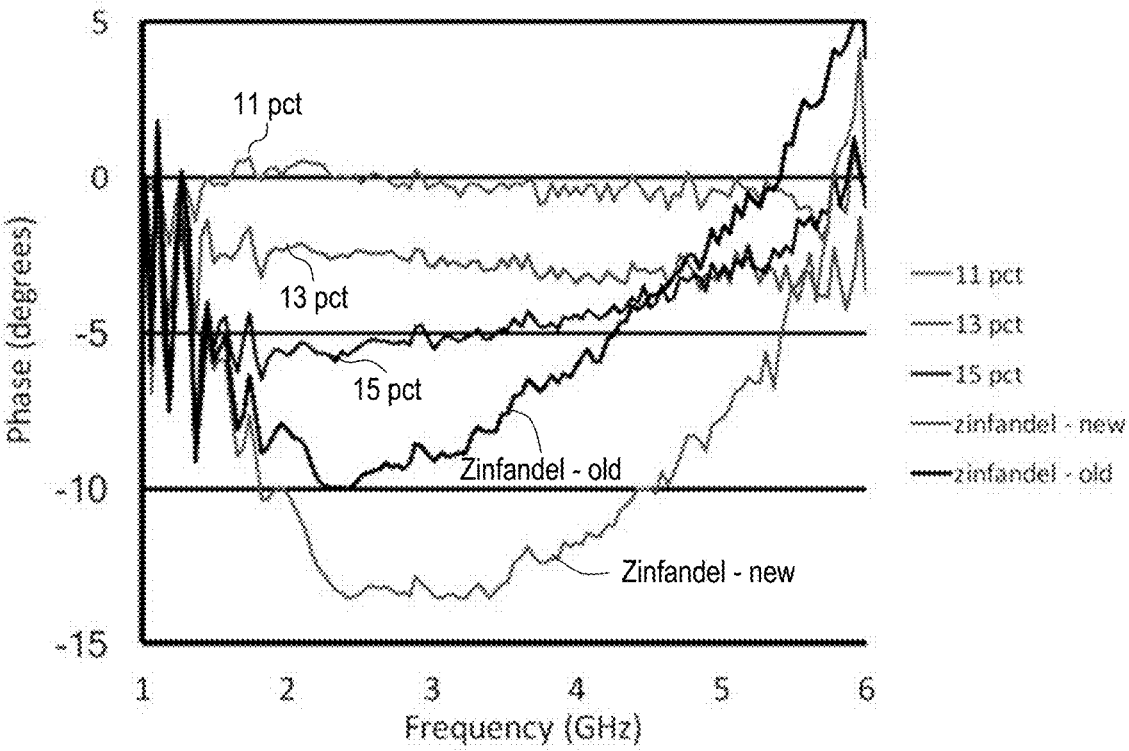
FIG. 9 is a plot of phase spectra obtained using the probe assembly of FIGS. 7A and 7B.

FIG. 9 is a plot of phase spectra obtained using probe assembly 700 and spectrum analyzer 750. The spectra plotted in FIG. 9 are examples of spectrum 170. FIG. 9 plots, for the same bottled liquids investigated in FIG. 8, the microwave phase detected by spectrum analyzer 750, via the probe associated with center conductor 712(2), as a function of the frequency of the microwave signal outputted by spectrum analyzer 750 via the probe associated with center conductor 712(1). Again, although some features are shared between the different types of liquids, different liquids have different phase spectra.

Figure 10:
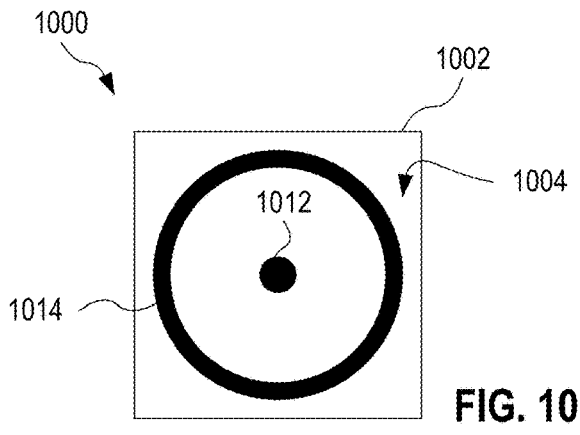
FIG. 10 illustrates a coaxial probe based on a flexible substrate, according to an embodiment.

FIG. 10 illustrates one coaxial probe 1000 based on a flexible substrate. Probe 1000 is an embodiment of either one of emission probe 110 and detection probe 120 and may be implemented in configurations 200 and 300. Probe 1000 includes a dielectric flexible substrate 1002, a center conductor 1012 on substrate 1002, and a circular outer conductor 1014 on substrate 1002. FIG. 10 is a view of a front side 1004 of substrate 1002. Outer conductor 1014 is centered about center conductor 1012 to form a coaxial probe having an axis that coincides with center conductor 1012 and is orthogonal to the plane of FIG. 10. Each of center conductor 1012 and outer conductor 1014 may be made of metal and may be plated, cast, adhered or otherwise deposited onto substrate 1002. Each of center conductor 1012 and outer conductor 1014 may be plated onto front side 1004. Alternatively, or in combination therewith, each of center conductor 1012 and outer conductor 1014 may be plated onto one or more vias between front side 1004 and a back side of substrate 1002.

FIG. 10 shows probe 1000 in a planar state. However, probe 1000 may be flexed out of the plane of FIG. 10. When method 400 is performed using probe 1000, steps 401 and 402 may include bending probe 1000 to conform to wall 192. In one use scenario, probe 110 is bent and held against wall 192 by a user or a robot. In another use scenario, probe 110 is bent and held against wall 192 at least in part by an adhesive.

Figure 11:
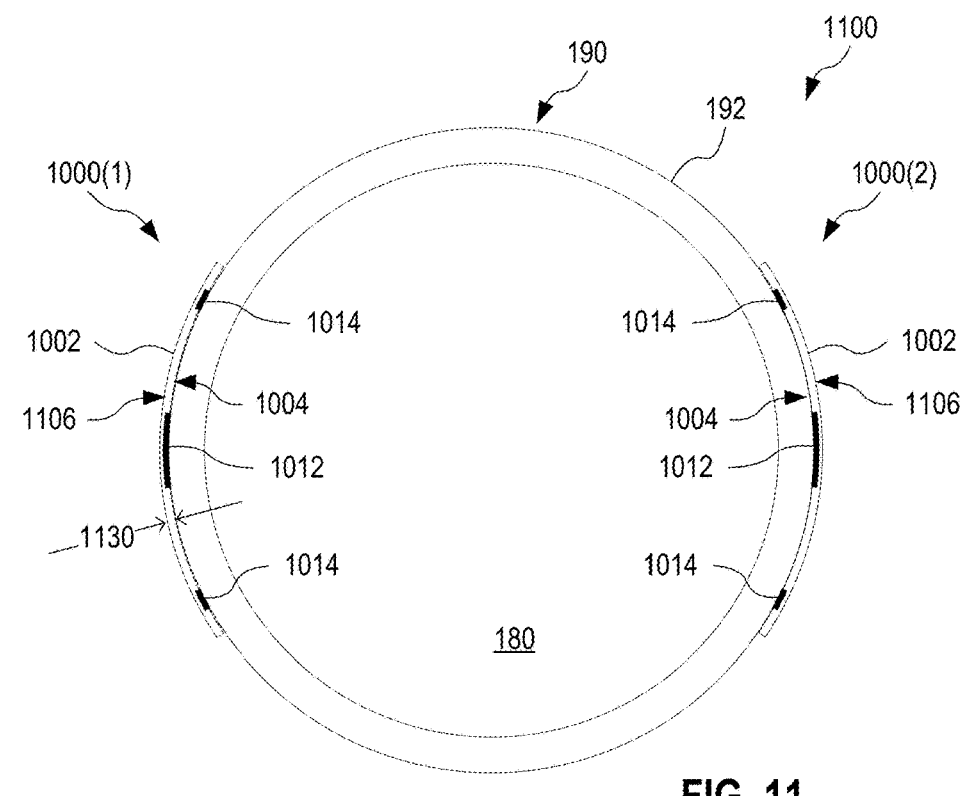
FIG. 11 illustrates a transmission-based configuration of an embodiment of the system of FIG. 1 that implements two instances of the probe of FIG. 10, according to an embodiment.

FIG. 11 illustrates one transmission-based configuration 1100 of an embodiment of system 100 that implements two probes 1000. Configuration 1100 is an example of configuration 200. In configuration 1100, two instances of probe 1000 are coupled to opposite sides of wall 192 of bottle 190 with front side 1004 of each probe 1000 facing wall 192. As an alternative to configuration 1100, two instances of probe 1000 may be positioned next to each other as in configuration 200.

Referring now to FIGS. 10 and 11 in combination, the dimensions of center conductor 1012, outer conductor 1014, and the portion of substrate 1002 therebetween may be similar to the dimensions of center conductor 512, outer conductor 514 and insulator 518 at end face 516 of probe 500. Substrate 1002 may have thickness 1130 (see FIG. 11) in the range between 0.0005 and 0.005 inches. Substrate 1002 is for example made of a polymer, such as polyimide or a derivate thereof.

Electrical connections to center conductor 1012 and outer conductor 1014 are not depicted in FIGS. 10 and 11. However, such connections may be made on a surface of substrate 1002 and/or through substrate 1002. For example, a metal-coated via through substrate 1002 may connect center conductor 1012 on a front side 1004 of substrate 1002 to a connection of a backside 1106 (see FIG. 11) of substrate 1002. Similarly, one or more metal-coated vias through substrate 1002 may connect outer conductor 1014 to a connection, e.g., a ground plane, on backside 1106 of substrate 1002. Without departing from the scope hereof, probe 1000 may include one or more additional flexible layers that are layered to a back side of substrate 1002 to form a laminated structure, and connections to center conductor 1012 and outer conductor 1014 may be formed on different levels of this laminated structure. Probe 1000 may utilize architectures disclosed in PCT Patent Application Publication no. WO 2012/155057, which is incorporated herein by reference in its entirety.

Figure 12:
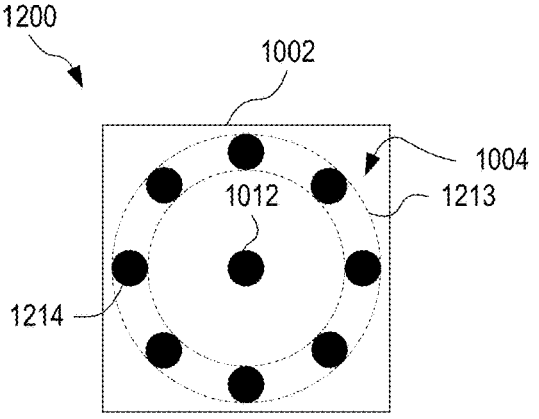
FIG. 12 illustrates another coaxial probe based on a flexible substrate, according to an embodiment.

FIG. 12 illustrates another coaxial probe 1200 based on a flexible substrate. Probe 1200 is similar to probe 1000 except for replacing circular outer conductor 1014 with a series of separate conductors 1214 located within a ring-shaped region 1213. Conductors 1214 cooperate to form an outer conductor that is coaxial with center conductor 1012. Each of conductors 1214 may coincide with a via through at least a portion of substrate 1002 to a connection, e.g., a ground plane, on the backside of substrate 1002 or on an intermediate layer in a laminated structure including substrate 1002.

Conductors 1214 may be evenly distributed along ring-shaped region 1213, as shown in FIG. 12, or unevenly distributed along ring-shaped region 1213. For example, a particularly large gap may exist between one pair of adjacent conductors 1214 to accommodate a transmission line to center conductor 1012 on the backside of substrate 1002. Probe 1200 may utilize architectures disclosed in PCT Patent Application Publication no. WO 2012/155057, which is incorporated herein by reference in its entirety.

Figure 13:
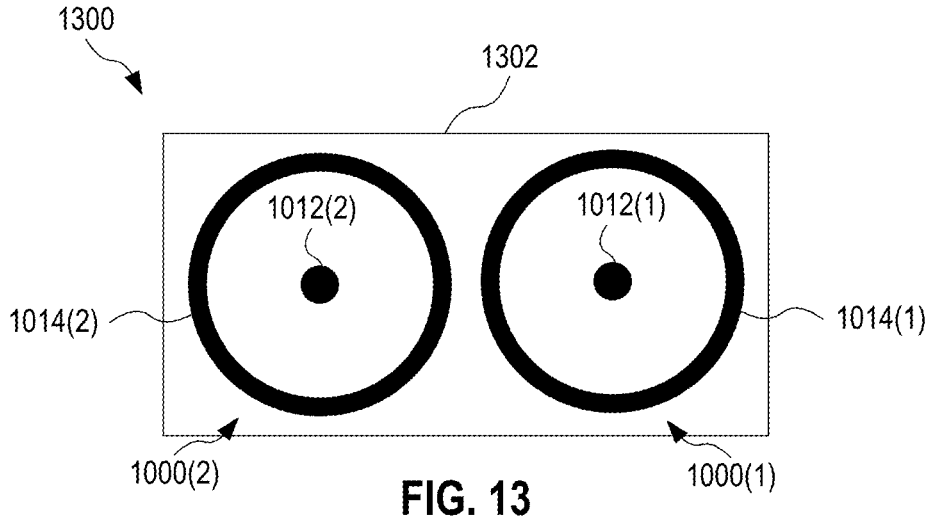
FIG. 13 illustrates a dual-coaxial flexible probe assembly, according to an embodiment.

FIG. 13 illustrates one dual-coaxial flexible probe device 1300. Probe device 1300 is an extension of probe 1000 to include two instances of probe 1000 on a common flexible substrate 1302. Without departing from the scope hereof, one or both of probes 1000 of probe device 1300 may be replaced by probe 1200.

Figure 14:
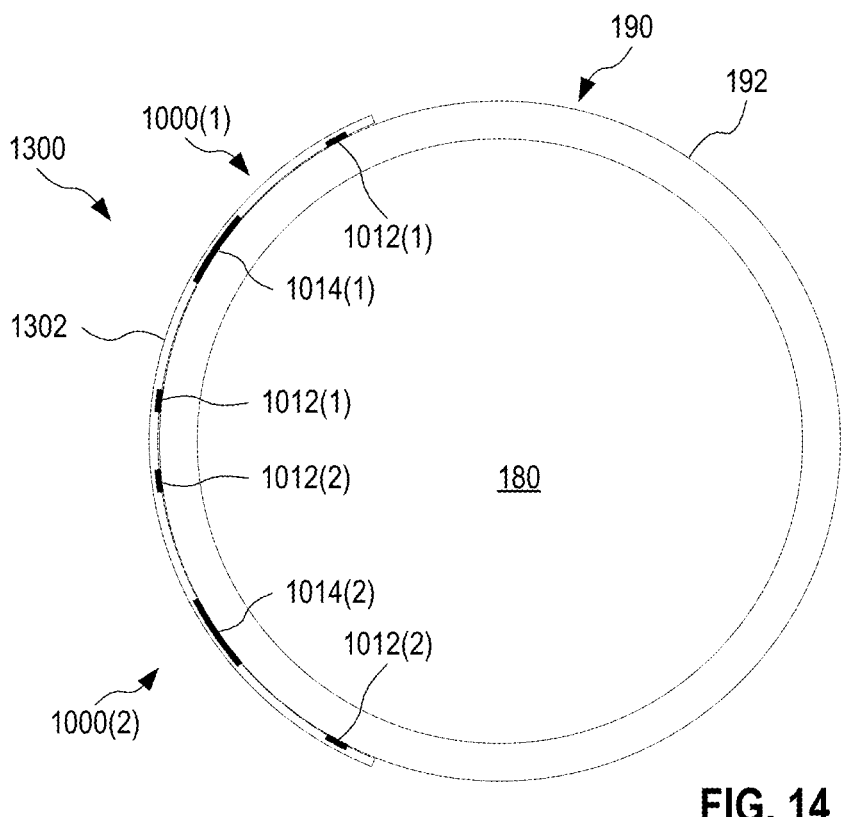
FIG. 14 illustrates an example use scenario of the probe assembly of FIG. 13.

FIG. 14 illustrates one example use scenario of probe device 1300, wherein probe device 1300 is configured according to side-by-side configuration 300. In embodiments of method 400 that utilize probe device 1300, steps 401 and 402 are performed simultaneously and may include bending probe device 1300 to conform to wall 192, as discussed above in reference to FIG. 4.

Without departing from the scope hereof, a single instance of any one of probes 500, 1000, and 1200 may be used in reflection mode for non-invasive microwave testing of wine 180 in bottle 190. In such reflection-mode based testing, the single probe is used for both emission and detection of microwave signal 160.

The phase and magnitude spectra determined by the system we describe herein are determined in large part by permittivity and conductivity of the wine, or other liquid, present in the bottles.

Figure 15A:
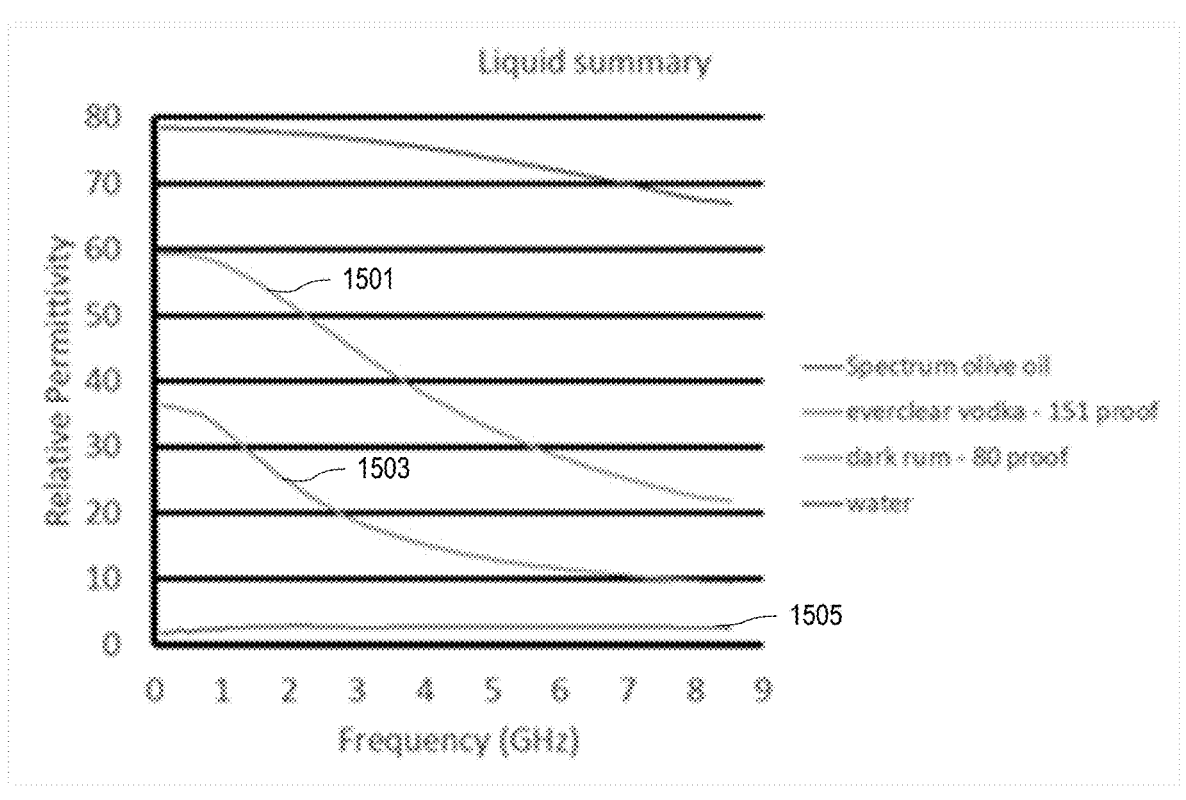
FIGS. 15A and 15B illustrate permittivity and conductivity, respectively, of water, 80-proof rum, and 151-proof vodka.
Figure 15B:
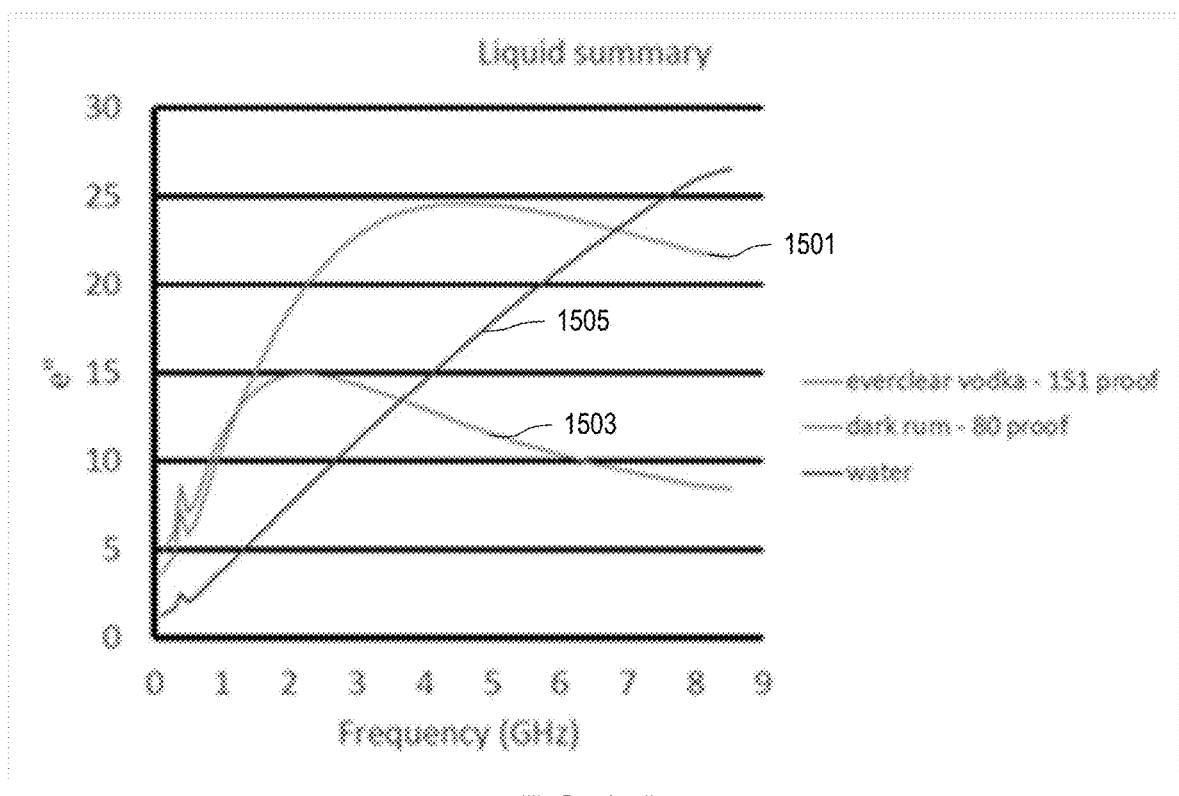

We have found that the system described herein is also applicable to noninvasive testing of liquid substances other than wine. In an experiment, as illustrated in FIGS. 15A and 15B, we have observed distinct and clearly measurable differences in permittivity and conductivity spectra between 80 proof dark rum 1501, water 1505, and 151-proof vodka 1503, indicating that the system is capable of distinguishing between some types of alcoholic beverages such as whiskeys, rums, vodkas, wine coolers, and others. The effect of bottle size, shape, permittivity and conductivity on the observed spectra was controlled during testing by using identical containers for each of these liquids.

Figure 16:
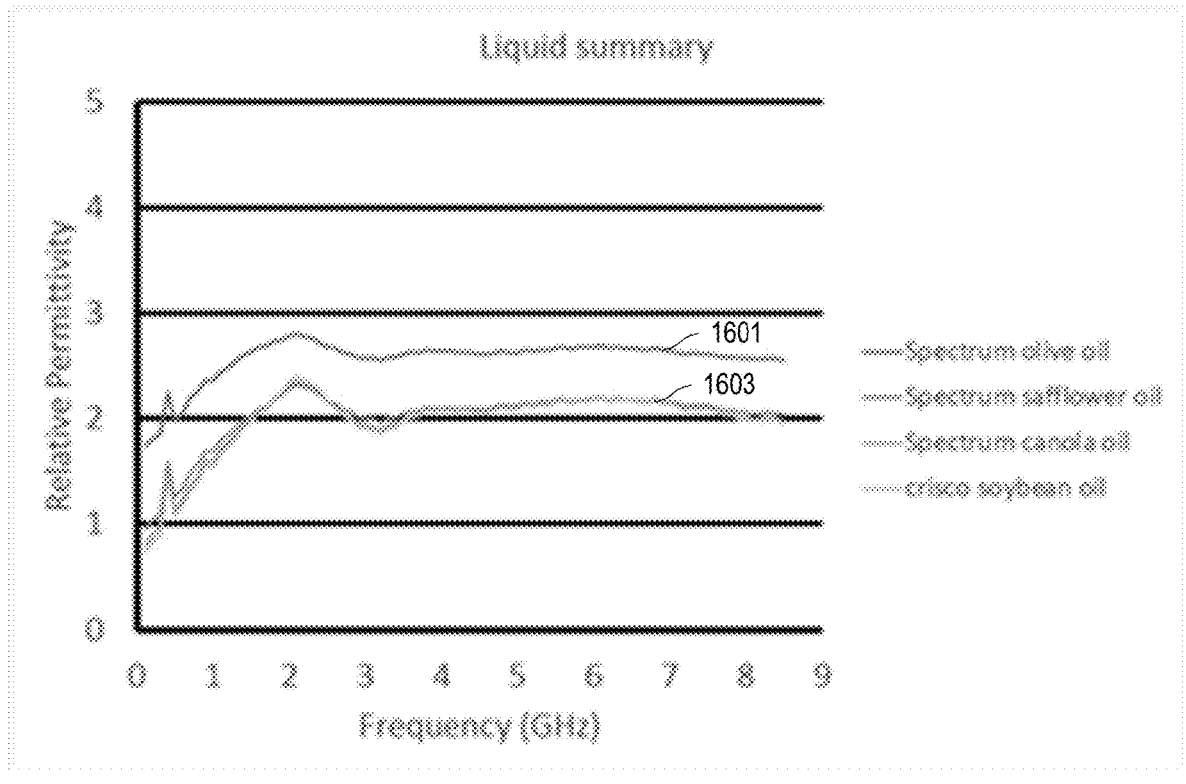
FIG. 16 illustrates permittivity spectra of several cooking oils, including olive oil and soybean oil.

In another experiment, as illustrated in FIG. 16, we found distinct differences in permittivity spectra between olive oil 1601 and some frequent adulterants that have been found as dilutants or substitutes for olive oil including canola oil, safflower oil, and soybean oil-almost superimposing on line 1603.

Figure 17A:
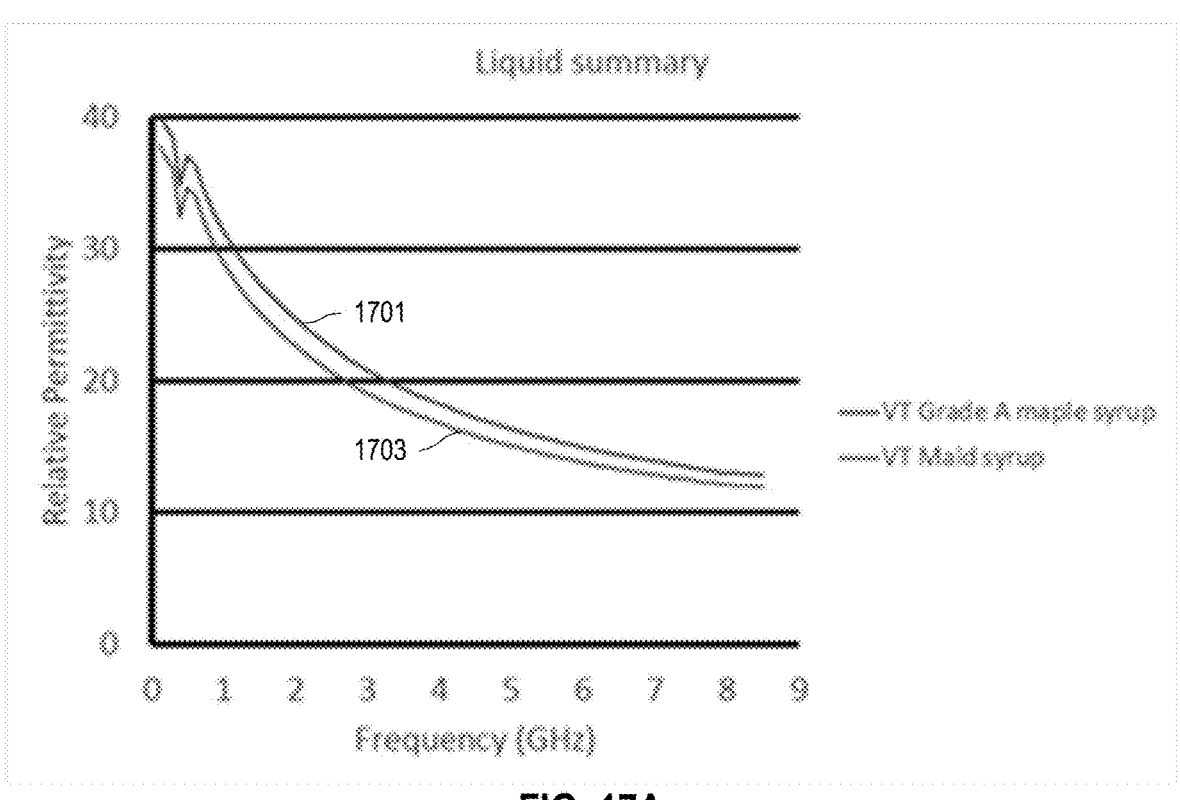
FIGS. 17A and 17B illustrate permittivity and conductivity spectra, respectively, of real and an imitation maple syrup.
Figure 17B:
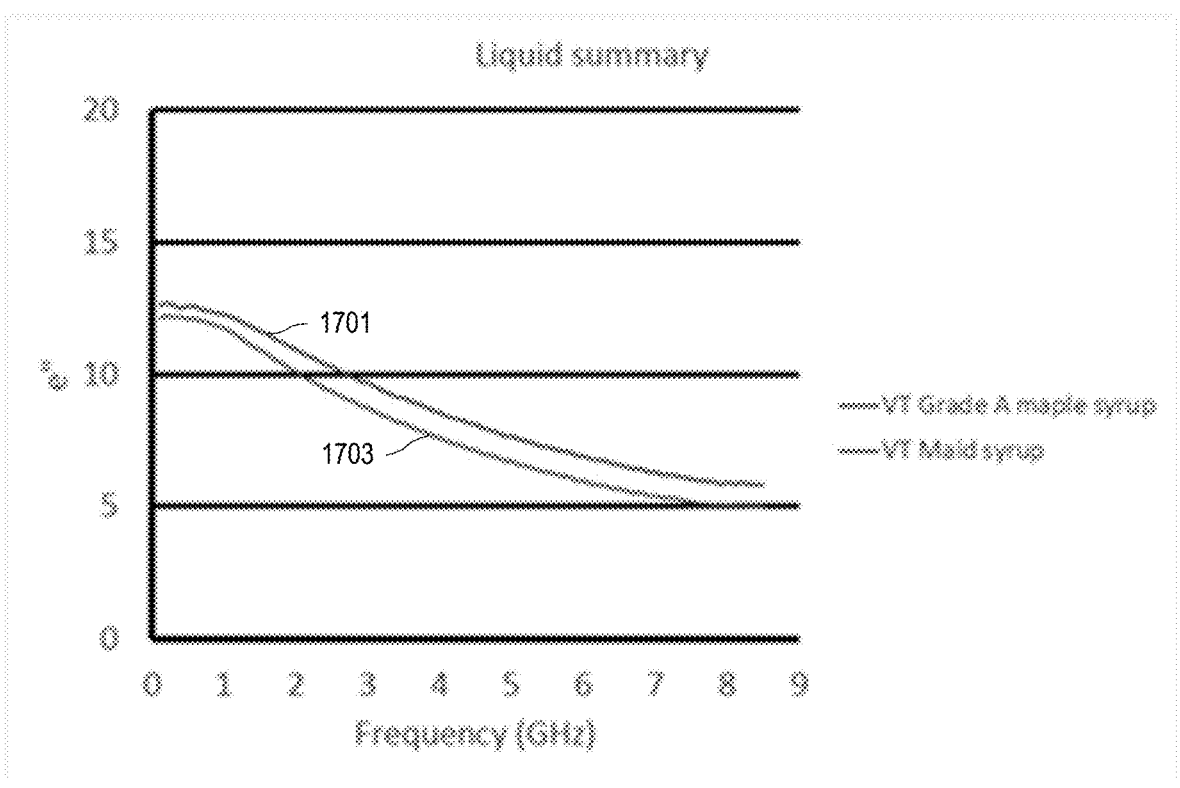

Another sometimes-counterfeited liquid is pure maple syrup, for which many imitations are made with corn syrup, sucrose syrup, or other syrups. In an experiment, as illustrated in FIGS. 17A and 17B, clear differences in permittivity and conductivity spectra were observed between real Vermont maple syrup 1701 and Vermont Maid syrup 1703, an imitation syrup.

Further, in the step of deducing properties 430 of the wine or other liquid, it is possible to input obtained spectra into a trained classifier, such as but not limited to a KNN (K-nearest neighbors) or a neural network, to deduce a composition of the liquid or a type of the wine. For example, we expect from the differences in spectra of FIG. 16, a classifier can be trained to distinguish olive oil from several common adulterants like soybean and canola oil. Similarly, from the differences shown in spectra of FIGS. 15A and 15B, it is expected that a classifier may be trained to distinguish between alcoholic beverages like 151 proof rum, whiskey, water, and wine; or to distinguish between real maple syrup and some common imitation maple syrups. Such a classifier may be trained on a training database that includes spectra from real olive oil or maple syrup, and spectra from a variety of other oils including soybean and canola oil or imitation maple syrups.

Combinations of Features

Features described above as well as those claimed below may be combined in various ways without departing from the scope hereof. For example, it will be appreciated that aspects of one probe, system, or method described herein may incorporate or swap features of another probe, system, or method described herein. The following examples illustrate possible, non-limiting combinations of embodiments described above. It should be clear that many other changes and modifications may be made to the methods and device herein without departing from the spirit and scope of this invention:

(A1) One system for non-invasive microwave testing a bottle of wine includes an emission probe for emitting a microwave signal through a wall of the bottle into the wine, and a detection probe for receiving at least a portion of the microwave signal from the wine via the wall.

(A2) In the system denoted as (A1), the emission probe and the detection probe may be identical and interchangeable.

(A3) In either of the systems denoted as (A1) and (A2), each of the emission probe and the detection probe may be a coaxial probe that includes a curved end face and a tapered coaxial transmission line leading to the curved end face, wherein the diameter of the tapered coaxial transmission line increases in direction toward the curved end face.

(A4) In the system denoted as (A3), the emission probe and the detection probe may be integrated in a common dual-coaxial probe assembly that includes (a) a conductive block having a cylindrical surface and forming two channels between the cylindrical surface and a back surface opposite the cylindrical surface, wherein diameter of each of the channels increases from the back surface to the cylindrical surface, (b) in a first one of the conical channels, a first center conductor and a first insulator separating the first center conductor from the conductive block, wherein the first center conductor and the first insulator cooperate with the conductive block and its cylindrical surface to form the emission probe, and (c) in a second one of the conical channels, a second center conductor and a second insulator separating the second center conductor from the conductive block, wherein the second center conductor and the second insulator cooperates with the conductive block and its cylindrical surface to form the detection probe.

(A5) In the system denoted as (A4), the first center conductor and the first insulator may cooperate to fill the first one of the conical channels, and the second center conductor and the second insulator may cooperate to fill the second one of the conical channels.

(A6) In either of the systems denoted as (A4) and (A5), the diameter of each of the first and second center conductors may increase from the back surface to the cylindrical surface, and the distance between the conductive block and each of the first and second center conductors may increase from the back surface to the cylindrical surface.

(A7) In any of the systems denoted as (A4) through (A6), the cylindrical surface may extend no more than 180 degrees about a cylinder axis of the cylinder.

(A8) In the system denoted as (A7), the first center conductor and the first insulator may be on a first side of a plane that includes the cylinder axis, and the second center conductor and the second insulator may be on a second side of the plane that is opposite the first side.

(A9) In the system denoted as (A8), the first and second center conductors may form mirror images of each other with respect to reflection in the plane.

(A10) In any of the systems denoted as (A4) through (A9), a shortest distance spanned by the conductive block along the cylindrical surface between the first and second insulators may extend less than 15 degrees about the cylinder axis.

(A11) In the system denoted as (A10), the diameter of each of the first and second insulators, along the cylindrical surface and in an azimuthal dimension relative to the cylinder axis, may extend at least 40 degrees about the cylinder axis.

(A12) In any of the systems denoted as (A4) through (A11), the first and second center conductors may be within ten degrees of being parallel to each other.

(A13) Any of the systems denoted as (A4) through (A12) may further include, on the back surface, a first coaxial connector for the emission probe and a second coaxial connector for the detection probe.

(A14) In any of the systems denoted as (A1) through (A13), each of the emission probe and the detection probe may be a coaxial probe based on a flexible substrate, axis of the coaxial probe being orthogonal to the flexible substrate.

(A15) In the system denoted as (A14), the flexible substrate may be dielectric, and the coaxial probe may include (i) a metallic center conductor plated on the flexible substrate and (ii) a metallic outer conductor plated on the flexible substrate in at least a portion of a circular region of the flexible substrate centered at the center conductor, wherein the metallic outer conductor is spaced apart from the metallic center conductor.

(A16) In the system denoted as (A15), the emission probe and the detection probe may be based on a common flexible substrate, with the metallic center and outer conductors of the emission probe being positioned in one region of the common flexible substrate and the metallic center and outer conductors of the emission probe being positioned in another region of the common flexible substrate.

(B1) One method for non-invasive microwave testing a bottle of wine includes (a) emitting, from an emission probe coupled to a wall of the bottle, a microwave signal through the wall and into the wine, and (b) receiving, from the wine via the wall, at least a portion of the microwave signal into a detection probe coupled to the wall.

(B2) The method denoted as (B1) may further include scanning the frequency of the microwave signal emitted in the step of emitting, and recording a spectrum of at least one of magnitude and phase of the at least a portion of the microwave signal received in the step of receiving.

(B3) In the method denoted as (B2), the step of recording may include recording a spectrum of both the magnitude and the phase.

(B4) Any of the methods denoted as (B1) through (B3) may further include coupling the emission and detection probes to the wall such that output area of the emission probe faces input area of the detection probe.

(B5) Any of the methods denoted as (B1) through (B3) may further include coupling the emission and detection probes to the wall such that an end face of the emission probe and an end face of the detection probe are (a) on a same half of circumference of the wall and (b) spaced apart from each other by a minimum distance that spans less than 15 degrees of the circumference of the wall.

(B6) Any of the methods denoted as (B1) through (B5) may further include coupling the emission and detection probes to the wall with a coupling gel between the outside surface and each of the emission and detection probes.

(B7) In any of the methods denoted as (B1) through (B6), each of the emission and detection probes may be a coaxial probe having an end face facing the wall.

(B8) In the method denoted as (B7), the coaxial probe may be tapered such that a diameter thereof increases in direction toward the end face.

(B9) In any of the methods denoted as (B1) through (B6), each of the emission and detection probes may be based on a flexible substrate.

(B10) The method denoted as (B9) may further include bending the emission and detection probes to conform to the wall.

Changes may be made in the above systems and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present systems and methods, which, as a matter of language, might be said to fall therebetween.

What is claimed is:

1. A system for non-invasive microwave testing a bottle of liquid, comprising:
   an emission probe for emitting a microwave signal through a wall of the bottle into the liquid; and
   a detection probe for receiving at least a portion of the microwave signal from the liquid via the wall; each of the emission probe and the detection probe being a coaxial probe that includes:
   a curved end face configured to fit adjacent a common bottle shape; and
   a tapered coaxial transmission line leading to the curved end face, diameter of the tapered coaxial transmission line increasing in direction toward the curved end face.

2. The system of claim 1, the emission probe and the detection probe being integrated in a common dual-coaxial probe assembly including:
   a conductive block having a cylindrical surface and forming two conical channels between the cylindrical surface and a back surface opposite the cylindrical surface, diameter of each of the conical channels increasing from the back surface to the cylindrical surface;
   in a first one of the conical channels, a first center conductor and a first insulator separating the first center conductor from the conductive block, the first center conductor and the first insulator cooperating with the conductive block to form the emission probe; and in a second one of the conical channels, a second center conductor and a second insulator separating the second center conductor from the conductive block, the second center conductor and the second insulator cooperating with the conductive block to form the detection probe.

3. The system of claim 2, diameter of each of the first and second center conductors increasing from the back surface to the cylindrical surface, distance between the conductive block and each of the first and second center conductors increasing from the back surface to the cylindrical surface.

4. The system of claim 3, further comprising a classifier trained to distinguish olive oil from an adulterant to the olive oil, the adulterant including one or more of soybean, safflower, and canola oil.

5. The system of claim 3, further comprising a classifier trained to distinguish between a plurality of alcoholic beverages.

6. The system of claim 3, further comprising a classifier trained to distinguish maple syrup from imitation maple syrup.

7. A method for non-invasive microwave testing a bottle of liquid, comprising:

emitting, from an emission probe coupled to a wall of the bottle, a microwave signal through the wall and into the liquid; and receiving, from the liquid via the wall, at least a portion of the microwave signal into a detection probe coupled to the wall;

scanning frequency of the microwave signal emitted in the step of emitting; and recording at least one spectrum of at least one of magnitude and phase of the at least a portion of the microwave signal received in the step of receiving.

8. The method of claim 7, the step of recording at least one spectrum comprising recording a spectrum of both the magnitude and the phase.

9. The method of claim 8, further comprising coupling the emission and detection probes to the wall such that output area of the emission probe faces input area of the detection probe.

10. The method of claim 9, each of the emission and detection probes being a coaxial probe having an end face facing the wall; the coaxial probes being tapered such that a diameter thereof increases in direction toward the end face.

11. The method of claim 8, further comprising:

using a trained classifier on the recorded spectra to deduce a composition of the liquid.

12. The method of claim 11, the classifier being adapted to distinguish olive oil from an adulterant to the olive oil, the adulterant including one or more of soybean oil, safflower oil, and canola oil.

13. The method of claim 11, wherein the classifier being adapted to distinguish maple syrup from imitation maple syrup.

14. The method of claim 11, the classifier is adapted to distinguish between a plurality of alcoholic beverages.

* * * * *